United States Patent
Waugh et al.

(10) Patent No.: US 8,849,449 B2
(45) Date of Patent: Sep. 30, 2014

(54) METHOD, SYSTEM AND APPARATUS FOR DISPENSING DRUGS

(75) Inventors: Donald Craig Waugh, Oakville (CA);
James Brandon Parrott, Bolton (CA);
Peter Gaspard Suma, Aurora (CA);
Michael Graves Mansell, Cedar Valley (CA)

(73) Assignee: MedAvail, Inc., San Francisco, CA (US)

( * ) Notice: Subject to any disclaimer, the term of this patent is extended or adjusted under 35 U.S.C. 154(b) by 1073 days.

(21) Appl. No.: 12/305,759

(22) PCT Filed: Jul. 11, 2007

(86) PCT No.: PCT/CA2007/001220
§ 371 (c)(1),
(2), (4) Date: Feb. 16, 2010

(87) PCT Pub. No.: WO2008/006203
PCT Pub. Date: Jan. 17, 2008

(65) Prior Publication Data
US 2010/0198401 A1      Aug. 5, 2010

Related U.S. Application Data

(60) Provisional application No. 60/819,622, filed on Jul. 11, 2006.

(51) Int. Cl.
| | |
|---|---|
| *G06F 17/00* | (2006.01) |
| *G07F 11/00* | (2006.01) |
| *G06Q 10/08* | (2012.01) |
| *G06F 19/00* | (2011.01) |
| *A61J 7/00* | (2006.01) |

(52) U.S. Cl.
CPC .......... *G07F 11/002* (2013.01); *G06F 19/3418* (2013.01); *A61J 2205/10* (2013.01); *A61J 7/0084* (2013.01); *A61J 2205/30* (2013.01); *G06Q 10/087* (2013.01); *G06F 19/3462* (2013.01); *A61J 2205/60* (2013.01)
USPC ............ 700/234; 700/237; 700/235; 700/236

(58) Field of Classification Search
USPC ................................. 700/237, 240, 234–236
See application file for complete search history.

(56) References Cited

U.S. PATENT DOCUMENTS

| | | | | |
|---|---|---|---|---|
| 5,883,370 | A * | 3/1999 | Walker et al. ................. | 235/375 |
| 6,871,783 | B2 * | 3/2005 | Kaafarani et al. ............. | 235/380 |
| 7,471,993 | B2 * | 12/2008 | Rosenblum ................... | 700/237 |
| 7,630,788 | B1 * | 12/2009 | Reese ........................... | 700/216 |
| 7,783,383 | B2 * | 8/2010 | Eliuk et al. .................... | 700/245 |
| 8,191,719 | B2 * | 6/2012 | Van Ooyen et al. ........ | 211/87.01 |

(Continued)

*Primary Examiner* — Michael K Collins
(74) *Attorney, Agent, or Firm* — DeSandro Law Group PLLC; Bradley K. DeSandro

(57) ABSTRACT

A method, system and apparatus is provided for dispensing drugs quickly, conveniently, securely, and accurately and at relatively less cost than traditional pharmacy-based dispensing systems. A script for a drug prescribed to a user is generated comprising a human readable description of the drug and the user or a machine readable description of the drug and the user. The script is provided to a robotic prescription dispensary operable to recognize either the human readable description or the machine readable description, and validate and dispense the drug accordingly. The robotic prescription dispensary includes a user interface, a tele conferencing or video conferencing means enabling communication between the user and a human validation agent, and a scanning means for capturing an image of the script. A method for managing inventory and distribution of drugs is also provided.

20 Claims, 8 Drawing Sheets

(56) References Cited

U.S. PATENT DOCUMENTS

| | | | |
|---|---|---|---|
| 8,267,310 B2 * | 9/2012 | Waugh et al. | 235/375 |
| 2004/0215369 A1 * | 10/2004 | Rosenblum | 700/235 |
| 2007/0043469 A1 * | 2/2007 | Draper | 700/231 |
| 2007/0112593 A1 * | 5/2007 | Daya | 705/2 |
| 2010/0051187 A1 * | 3/2010 | Willick et al. | 156/238 |
| 2010/0145506 A1 * | 6/2010 | Waugh et al. | 700/231 |
| 2010/0198401 A1 * | 8/2010 | Waugh et al. | 700/237 |
| 2010/0268380 A1 * | 10/2010 | Waugh et al. | 700/239 |
| 2010/0305975 A1 * | 12/2010 | Daya et al. | 705/3 |

* cited by examiner

METHOD, SYSTEM AND APPARATUS FOR DISPENSING DRUGS

PRIORITY

This application claims the benefit of U.S. Provisional Patent Application No. 60/819,622, filed 11 Jul. 2006.

FIELD OF THE INVENTION

The present invention relates to method, system and apparatus for dispensing drugs.

BACKGROUND OF THE INVENTION

The traditional means of dispensing drug involves a doctor meeting with a patient and prescribing drugs or drugs based on a particular diagnosis. A prescription is then hand written or printed, and generally must be signed. The doctor generally updates the patient's paper file, and the patient takes their prescription to a pharmacy to be filled.

This traditional system of dispensing drug is considered relatively slow, inefficient, inconvenient, and various security or accuracy problems can arise. For example, a pharmacy can encounter a problem with a prescription because of the illegibility of the handwriting, which requires a call back to the doctor for clarification. There is also a potential problem where the wrong prescription is filled if the pharmacy does not do the call back to clarify a prescription. Further, potential adverse drug interactions are dependant on the doctor or pharmacist manually researching or knowing the interactions in order to recognize the possible issues and alter a prescription on that basis. Because drugs have a finite lifespan, there are also a number of inventory management issues which have yet to be addressed by current drug dispensing methodologies.

In view of these and other problems, a novel method, system and apparatus for dispensing drugs is desirable.

SUMMARY OF THE INVENTION

The present invention provides a method, system and apparatus for dispensing drugs quickly, conveniently, securely, accurately and at less relative cost than traditional pharmacy-based dispensing systems.

In one aspect of the present invention, a method, system and apparatus for dispensing drugs enables doctors to prescribe drugs to patients by generating a script. The script is a unique identifier comprising one or more data elements. The unique script in turn allows a patient to fill their prescription via a robotic prescription dispenser, referred to as a "dispensary". The dispensary is operable to recognize the one or more data elements, and the drugs are dispensed on that basis.

The script can comprise two data components, for example: (a) human readable descriptions for a pharmacist to dispense the prescribed drugs; and (b) machine readable descriptions for the dispensary to dispense the prescribed drugs. The two components allow the patient choice when filling their prescription.

According to another aspect of the present invention, the dispensary can be located in the doctor's office or clinic and can be electronically linked to a computer used by the doctor, either directly or via a server. As a result, the present invention allows a patient to obtain prescribed drugs without having to attend a pharmacy or drug store.

According to another aspect of the present invention, the dispensary can be linked to a pharmacist via a communication medium such as a multimedia video conferencing technology. The pharmacist can monitor the dispensary and approve each prescription.

According to an embodiment of the present invention, a system for dispensing drugs comprises: a server computer; a database of patient information linked to the server computer; a computer input means linked to a server computer, wherein the computer input means is operable to generate a script for a drug prescribed to a user, wherein the script comprises a plurality of data elements, the plurality of data elements including: a human readable description of the drug and the user; or a machine readable description of the drug and the user; and a robotic prescription dispensary operable to recognize either the human readable description or the machine readable description of the drug and the user, wherein the robotic prescription dispensary is linked to the server computer enabling cross-referencing between the machine readable description and the patient information to validate dispensing the drug to the user on the basis of the machine readable description, and wherein the robotic prescription dispensary comprises: a user interface; a tele conferencing or video conferencing means enabling communication between the user and a human validation agent to validate dispensing the drug to the user on the basis of the human readable description; and a scanning means for capturing an image of the script so that it can be viewed by the human validation agent.

For example, the doctor uses the computer input means (for example, a tablet computer) which is linked to the server to input the appropriate prescription information, or accept certain prescription information as being applicable in the particular case. The doctor enters the prescription into the tablet computer which displays the patient information, e.g., drug history, insurance coverage, etc. To the extent that the present invention enables access to personal information, the system incorporates known technology for maintaining privacy. In a particular embodiment of the present invention, a printer module is provided to print the script as a paper print-out comprising text and a machine readable bar code or the like. Alternatively, the prescription information can be loaded on a smart card or the like.

In a particular aspect of the present invention, the system includes or is linked to a database for storing, compiling and enabling retrieval of relevant patient information, for example, the patient's personal information such as name and address, as well as health-relevant information such as diagnostic history and drug history. Access to the database may be provided to both the doctor and to the dispensary via the server, via a secure connection, or via a link between the system and a clinic's existing clinic management system or patient database.

In a particular aspect of the method of the present invention, a patient seeking to fill a prescription provides the script to the dispensary, the dispensary having a user interface. At each step, the user interface provides detailed and clear instructions to guide the patient. An authentication means confirms the identity of the patient, for example, by prompting for a personal identification number or by biometric means or by associating certain questions to answers provided by the patient that identify the patient to the robotic prescription dispenser. Once the patient is recognized, the dispensary will prompt the patient for the script.

The dispensary is operable to process the script, and optionally verifies information with the server and the database. In a particular embodiment, the dispensary interfaces with the server, or with an adjudication server, to adjudicate any insurance claim and to determine the amount payable by the patient. The patient either accepts or rejects the transaction. If the transaction is accepted, the dispensary will interface with the server, or with a transaction server, to transact a payment, for example, by prompting the patient for credit card information. The dispensary is operable to print prescription labels and receipts. The dispensary confirms that the medication is correct and drops it into a dispensing area within the dispensary while retaining the script in a lock box. The dispensary verifies that the medication has been retrieved. The robotic prescription dispenser optionally prints or provides educational materials to the patient relevant to the particular prescription drugs being dispensed.

According to yet another aspect of the present invention, a method for managing the distribution of a drug is provided comprising receiving the drug, retrieving or defining standard operating procedures applicable to the drug, applying the standard operating procedures to the drug, recording drug attributes, applying RFID as means for tracking the drug, and placing the drug into distribution. Preferably, radio frequency identification ("RFID") device technology is implemented to track and control the dispensing of drug throughout the supply chain, including inside the robotic prescription dispensary. Inventory management can also be achieved both for the robotic prescription dispensary and one or more warehouses where the drugs are stockpiled prior to being stocked into a robotic prescription dispensary.

BRIEF DESCRIPTION OF THE DRAWINGS

A detailed description of one or more embodiments is provided herein by way of example only and with reference to the following drawings, in which.

Figure 1:
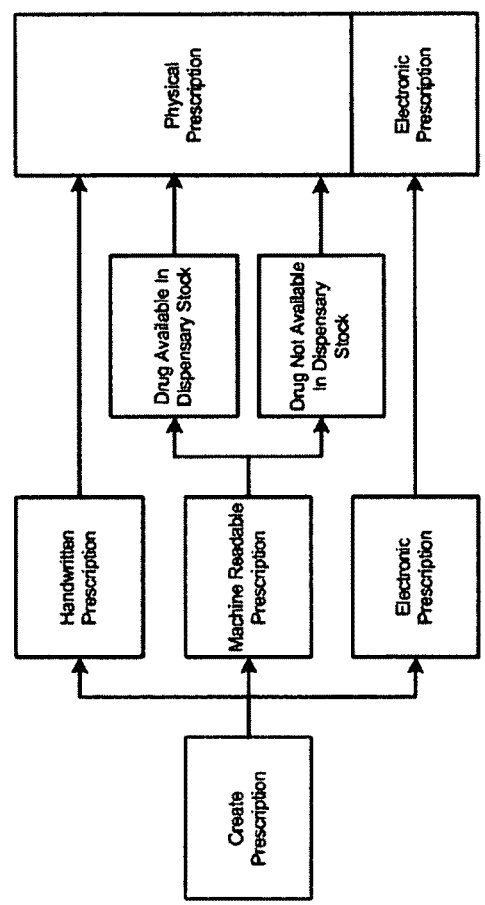
FIG. 1 is a flowchart illustrating steps for generating a prescription.

In the drawings, one or more embodiments of the present invention are illustrated by way of example. It is to be expressly understood that the description and drawings are only for the purpose of illustration and as an aid to understanding, and are not intended as a definition of the limits of the present invention.

DETAILED DESCRIPTION OF THE INVENTION

The term PharmaTrust™ as used herein denotes systems, methods and apparatuses in accordance with one or more embodiments of the present invention.

The present invention provides a method, system and apparatus for dispensing drugs quickly, conveniently, securely, accurately and at less relative cost than traditional pharmacy-based dispensing systems.

In one aspect, the present invention is a method for dispensing drugs comprising generating a script for a drug prescribed to a user, the script comprising a plurality of data elements, wherein the plurality of data elements include (i) a human readable description of the drug and the user; or (ii) a machine readable description of the drug and the user, providing the script to a robotic prescription dispensary operable to recognize either the human readable description or the machine readable description, authorizing dispensing the drug to the user based on a validation means, and dispensing the drug to the user with the robotic prescription dispensary. The two components of the script and the ability of the dispensary to recognize regular prescriptions and machine readable prescription compatible with the dispensary allow the patient choice when filling their prescription.

According to another aspect of the present invention, the robotic prescription dispensary is linked to the server computer enabling cross-referencing between the machine readable description and the patient information to validate dispensing the drug to the user on the basis of the machine readable description. The robotic prescription dispensary may also comprise a user interface, a tele conferencing or video conferencing means enabling communication between the user and a human validation agent, and a scanning means for capturing an image of the script so that it can be viewed by the human validation agent, e.g., a licensed pharmacist. The pharmacist can monitor the dispensary and approve each prescription, if desired.

According to another aspect of the present invention, the robotic prescription dispensary can be located in the doctor's office or clinic and can be electronically linked to a computer input means used by a doctor prescribing a drug to a patient, for example, either directly or via a server. As a result, the present invention can allow a patient to obtain prescribed drugs without having to attend a pharmacy or drug store.

In one embodiment, a system in accordance with the present invention comprises a server computer, a database of patient information linked to the server computer, a computer input means linked to the server computer operable to generate the script for a drug prescribed to a user, and the robotic prescription dispensary operable to recognize either a human readable description or a machine readable description in the script, enabling cross-referencing between the machine readable description and the patient information to validate dispensing the drug to the user on the basis of the machine readable description, the robotic prescription dispensary including a user interface, tele conferencing or video conferencing means enabling communication between the user and a human validation agent to validate dispensing the drug to the user on the basis of the human readable description, and a scanning means for capturing an image of the script so that it can be viewed by the human validation agent.

A doctor in a clinic can use the computer input means (for example, a tablet computer) linked to the server to input the appropriate prescription information, or accept certain prescription information from the database as being applicable in the particular case for a particular patient. The doctor can enter the prescription into the tablet computer which displays the patient information, e.g., drug history, insurance coverage, etc. A printer module can print the script as a paper print-out.

The server computer and database enable storing, compiling and retrieval of relevant patient information, for example, the patient's personal information such as name and address, as well as health-relevant information such as diagnostic history and drug history. Access to the database can be provided to both the doctor and the robotic prescription dispensary via the server, via a secure connection, or via a link between the system and a clinic's existing clinic management system (see reference numeral 54 in FIG. 4) or patient database.

According to another aspect of the present invention, the user interface of the robotic prescription dispensary provides detailed and clear instructions to guide the user. An authentication means confirms the identity of the patient, for example, by prompting for a personal identification number or by biometric means or by associating certain questions to answers provided by the patient that identify the patient to the robotic prescription dispensary, and cross-referencing this information with the patient information stored on the database. Once the patient is recognized, the robotic prescription dispensary will prompt the user for a script. The robotic prescription dispensary processes the script either by a human validation agent, e.g., a licensed pharmacist, reviewing the human readable description of the drug and/or processing the machine readable description, e.g., a barcode, if applicable. This information can be verified with the server and the database. The robotic prescription dispensary may also interface with the server to adjudicate an insurance claim and determine the amount payable by the patient. The patient either accepts or rejects the transaction. If the transaction is accepted, the robotic prescription dispensary will interface with the server to transact a payment, for example, by prompting the patient for credit card information. Prescription labels and receipts are printed. The robotic prescription dispensary preferably confirms that the drug is correct and drops it into a dispensing area while retaining the script in a lock box. The robotic prescription dispensary verifies that the drug has been retrieved. The robotic prescription dispensary optionally also prints or provides educational materials to the patient relevant to the particular prescription drugs being dispensed.

Although the term "doctor" is used herein to define the individual prescribing drugs to a patient, it should be understood that the present invention contemplates use by any health care professional who is capable of prescribing drugs, such as a dentist or a nurse, for example.

With reference to FIG. 1, the following describes an example of the process of prescribing a drug using a computer input means. According to one particular embodiment, the computer input means can be a prescribing application resident on a personal computer, the computer equipped with a printer. The doctor examines the patient, and determines the drug to be prescribed. The doctor logs into the prescribing application, which can be a custom developed software application or a modified version of an existing prescribing application. User authentication can be performed via user name and password, biometric authentication, smart card, or any other appropriate means. The doctor's profile includes information and preferences that can impact the behaviour of the prescribing system (favourite drug lists, notification preferences, etc.).

Once a "create prescription" screen is displayed, the doctor can select a patient from the dropdown list. This list displays all patients currently checked in to the clinic, and also has the capability to search the clinic's entire patient list or add a new patient. Patient demographic and historical information are retrieved with the patient profile (e.g., contact information, benefits coverage, prescription history, etc.). Patient information can be drawn in real time from either an existing clinic management system (see reference numeral 54 in FIG. 4) in use at the clinic, a patient database or other such system in use by the clinic or a central server and database, discussed below. Links to external systems are generally facilitated by standard data-sharing methods such as direct database access or Application Programming Interface (API) integration.

Once the patient has been selected, the doctor selects a drug to prescribe. The drug dropdown list can be displayed in categories to simplify drug selection. For example:

Patient Drug—this section displays the previous n number of drugs prescribed to the patient by any doctor using the system. This information can be limited to only those doctors associated with a given clinic or chain if regulations or doctors preference dictates so.

Doctor's Favourites—this section displays a set of drugs commonly prescribed by the doctors in question. The list can be drawn either from a defined list set using the administration console of the prescribing system, or be dynamically based on the prescribing history of the doctor in question.

Dispensary—this section displays drug that is currently available in the local dispensary inventory. The prescribing system performs a real time inventory check to determine which items should be displayed.

All Approved Drug—this section displays a list of all drug approved for use by the regional authorities (e.g. for use in the U.S., Canada, etc.). This list is typically drawn from a standard drug database commercially available within a given jurisdiction.

The drug list generally displays the following information:

Drug Name

Available generic substitutions, with preference given to those generic drugs currently in the dispensary inventory.

The standard SIG (patient instructions e.g. "take one tablet twice daily") for the drug, which can be determined by either a pre-set list or by prescription history, as outlined herein.

A graphic indicator or icon used to indicate that a given drug is currently in stock in the local dispensary. This indicator can be used across any or all drug categories.

Upon selection of a drug, the system may determine whether there is an appropriate generic substitution available. If so, the doctor is presented with a generic substitution request, containing information about the requested substitution. If the doctor approves the substitution, the generic equivalent drug is selected in place of the brand-name drug. If the doctor denies the substitution, the originally selected drug is entered, and the 'no substitution' flag is set on that drug for the prescription.

Generally, any number of drugs (or items) can be added to a given prescription. For each item added to a prescription, a drug interaction check is performed. This is typically completed using information available in the standard drug database from which the list of drugs is drawn. This check can be made against other drug items included the prescription, drug prescribed to the patient in the past, or even against any known allergies associated with the patient in the prescribing system as determined by the preferences of the doctor using the prescribing system. In the case, where no interactions with other drug are found, the prescribing flow proceeds as normal. If a potential interaction is detected, a visual and/or audible alert is used to inform the doctor. Information on the interaction is provided on-screen, and the doctor has the opportunity to select another drug, or proceed with the prescription as is.

The doctor then enters the total quantity to be dispensed (e.g., 30 tablets). The doctor can enter any quantity desired, or use a dropdown or other type of list provided in the prescribing application. Generally, the dropdown list will display quantities available in the local dispensary at the top of the list. These quantities will be displayed with an associated icon or indicator to inform the doctor that the quantity is available in the dispensary.

The doctor can enter or select the SIG (patient instructions) for the drug. When a drug has an associated standard SIG, it will be automatically populated in the SIG field. This functionality delivers ease-of-use for the doctor, and also drives the concept of standard dosage prescribing, which is supported by pharmacists and desirable for the standardization of drug management. The doctor should have the ability to edit or replace the SIG for any given drug at any time. Generally, this capability is provided via free-text editing of the SIG field.

Standard SIG codes can be determined in a number of ways. Even within the same application, different methods of determining standard SIG can be utilized for different categories of drug (or different lists of drug e.g. patient drug, doctor's favorites, dispensary, all approved drug, etc.). For example:

Drug previously prescribed to a given patient can have its standard SIG assigned as prescribed in the patient's past prescription. The SIG could be as prescribed by the doctor currently using the system, any doctor at the local clinic, or even any doctor throughout the system, as set in the doctor's preferences.

The standard SIG could alternatively be determined based on a pre-set setting for the drug associated with either a single doctor or multiple doctors.

In another implementation or other drug category in the same implementation, the standard SIG for a given drug could be determined by the prescribing history of the doctor. In this case, the standard SIG could be re-assigned to match the previous SIG used for the drug by that doctor, or follow the prescribing habits of the doctor to match the most commonly selected SIG for the drug in question.

An external database of standard SIG codes could be used as well (e.g., a list provided with the standard drug database mentioned above).

In general, when selecting a SIG, a list of common choices should be presented to the doctor via a dropdown list or other such control.

Certain drugs may require special authorization for one reason or another. The system should have the capability to facilitate required secondary authorization during the prescribing process.

As an example, the Province of Ontario Canada, under its Ontario Drug Benefits (ODB) Program has designated certain drugs as "limited Use" drugs. These drugs require special authorization from the doctor (based on the clinical diagnosis for which they are being prescribed) in order for the drug to eligible for benefits coverage under the ODB program. In this case, the authorization code is drawn from a list of codes pre-determined by the Ontario government.

In one particular implementation, the benefits information in the patient profile designates the patient as a patient under the ODB program. Therefore, when a drug is selected, it is compared with the list of limited use drugs. If it is not on the list, the process continues normally. If the drug is on the limited use list, the doctor is presented with a list of possible medical conditions to which a limited use code has been assigned. As each drug could have multiple codes, the codes are displayed with explanations of each specific condition for which a code may be assigned to the drug. The doctor can then select the appropriate code; if no code matches the diagnosis, the doctor selects "no limited use code". In this way, the limited use codes for each drug are added to the prescription entry as required. Upon printing of the prescription, the limited use codes will be printed along with the other required drug information. This information can then be used when submitting a benefits claim to the ODB program.

The doctor can use the prescribing application to enter all required prescription information for the drug in question (e.g., the number of repeats, special instructions, etc.). When all required information has been assigned to the drug item, the doctor adds it to the prescription. Typically, the process outlined above can be repeated to add multiple drug items to a given prescription.

When all desired items have been added to the prescription, the doctor will typically print a script and provide it to the patient. The script can take a number of forms, but will contain a unique machine readable identifier that is associated with the prescription ID number created by the prescribing system. The identifier can be printed as text and/or a bar code, or saved to an RFID tag.

Figure 2:
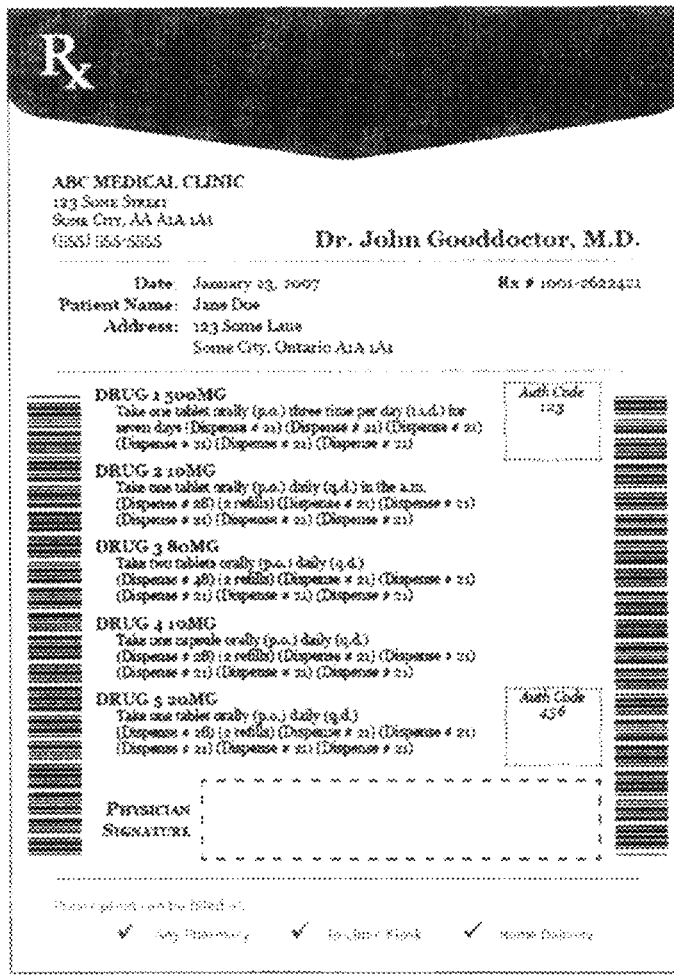
FIG. 2 illustrates an example of a script.

An example of a script is shown in FIG. 2.

It should be understood that according to a particular aspect of the present invention the script will preferably contain a human readable description and a machine readable description for use at the dispensary. The human readable description is for use in a traditional pharmacy. This provides the patient with choice in where they may have the prescription filled.

The prescription printout will contain all information required by the jurisdiction (e.g., names and addresses of the patient and doctor, date of prescribing, drug name and form, SIG and special instructions, etc.). In addition, where required, it will be signed by the doctor.

Ideally, the script will inform the patient as to where it can be filled. For example, as shown in FIG. 2, three possible alternatives are provided based on the drug type and availability: Any Pharmacy, In-clinic Dispensary and Home Delivery. This is provided to ensure that the patient understands their options in filling the prescription.

In certain circumstances, it is possible that not all of the items on a given prescription can be filled at the local dispensary. In these cases, the prescribing application will preferably group the drug items based on availability in the dispensary, and print those that are available at the dispensary on a separate printout(s) from those that are not available at the local dispensary. Ideally, each of these prescription printouts will be assigned a unique identification number in support of solid data management practices.

It is also possible that a prescription with a large number of items will not be able to be printed on a single printout. In this case, the items are typically spread across multiple prescription printouts, each with a unique ID number, as above.

Alternatively, as shown in FIG. 1, the doctor can create an electronic prescription with no associated script. In this case, the patient would access the prescription at the dispensary via an ID number (typically their health card or account number) or chit provided by the doctor. The electronic prescription could be digitally signed via digital signature or any other appropriate means. The prescription information would be transferred and processed throughout the system in the same manner as described for handling printed prescriptions, but without the need for the physical prescription printout.

Once the prescription has been printed, or submitted in the case of an electronic prescription, the prescription information is posted to central server, discussed below. In a typical implementation of the invention, it is also posted to the patient's history in the particular clinic's standard pharmacy management system. In this manner, the prescription information can be accessed, under the appropriate personal privacy and data security policies, by any dispensary and/or the patient support call centre. Access to prescriptions from a given doctor or clinic can also be limited to the dispensary or dispensaries local to that clinic, based on legal or regulatory constraints of the region or the preferences of the doctor or clinic.

Figure 3:
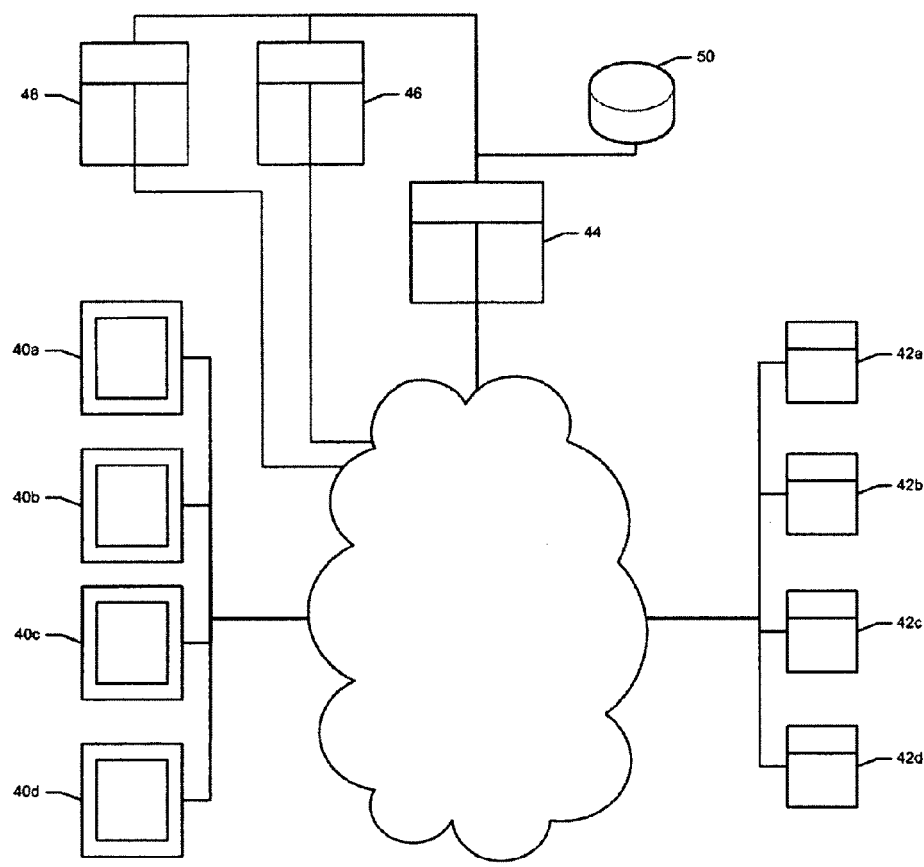
FIG. 3 is a system diagram according to an embodiment of an aspect of the present invention.

FIG. 3 illustrates a representative system implementation of the present invention. The system includes a central server (44) that includes or is linked to resources that are operable to provide the functionality described below, including but not limited to quality control, quality monitoring, inventory management, distribution management and audit functionality. The central server (44) is linked to one or more databases (represented as database (50) in FIG. 3. The database (50) and the central server (44) (and associated utilities) co-operate to store and to enable the retrieval of various data related to the operation of the system components of the invention. Depending on privacy laws and policies, regulatory requirements, and other factors, the database (50) may include patient data in certain specific implementations of the present invention.

The system also includes a plurality of computers associated with one or more doctor's offices, and used to access the functions described herein. These computers are shown in FIG. 3 as computers (42a) (42b) (42c) (42d). These computers can be any manner of computer device including a desktop computer, computer terminal, personal digital assistant (linked to other computer resources or otherwise), laptop computer, or tablet computer. Computers (42a) (42b) (42c) (42d) may also be linked to the computer network, thereby providing connectivity to the other system components to enable the functions described below. Computers (42a) (42b) (42c) (42d) may include or be linked to the resources described below in connection with FIG. 4.

The system also includes one or more dispensaries, as shown in FIG. 3. In FIG. 3, a plurality of dispensaries is shown as (40a) (40b) (40c) (40d). The dispensaries (40a) (40b) (40c) (40d), in one particular implementation thereof, include the resources described below, including in connection with FIG. 5. The dispensaries (40a) (40b) (40c) (40d) are also linked to the computer network, thereby providing connectivity to the other system components to enable the functions described below.

The central server (44), via the computer network, is operable to manage the operation of the dispensaries (40a) (40b) (40c) (40d), including as described below. In a specific aspect of the present invention, the central server (44) is operable to control the operation of the dispensaries (40a) (40b) (40c) (40d) remotely.

In a particular aspect of the present invention, the central server (44) and the computers (42a) (42b) (42c) (42d) may be interoperable, via the computer network, in order to enable provisioning of the computers (42a) (42b) (42c) (42d), for example, in order to provide access to resources, software updates, data services and otherwise, as web services provided by the central server (44) to the computers (42a) (42b) (42c) (42d).

The computers (42a) (42b) (42c) (42d) and the dispensaries (40a) (40b) (40c) (40d) may be interoperable, via the computer network, to enable a doctor or designate of the doctor to initiate drug dispensing involving one or more of the dispensaries (40a) (40b) (40c) (40d), including as detailed below.

The present invention contemplates different variations in terms of the relationships of medical professionals or their designate and particular dispensaries. Generally speaking, the present invention contemplates the central server (44) being operable to define and control which of the dispensaries are associated, from time to time, with computers that are part of the system or recognized by the system. For example, a single doctor or her designate and a single corresponding computer (for example (42a)) may be associated with one or more of the dispensaries (for example (40a) or both (40a) and (40b)). The doctor or her designate may be associated with a single dispensary or multiple dispensaries, for example, if there is more than one dispensary in the doctor's building, or if a particular dispensary (42a) has a more extensive stock, while (42b) constitutes a closer dispensary with less stock, it might be desirable to associate more than one dispensary with computer (40a). It is possible that the dispensary could be associated with solely with a particular doctor's office, depending on volume for example. Typically, however multiple doctors or their designate will be associated with a single dispensary located close their offices of the doctors in question, often in a medical building.

The system may also include an adjudication server (46), optionally linked to the central server (44) or to the computer network. The adjudication server (46) may be associated with a third party and not with the operator of the central server (44). The adjudication server (46) may be operable to engage in a number of transactions related to the adjudication of insurance claims related to delivery of drugs by operation of the drug dispensaries (40a) (40b) (40c) (40d) as described below.

The system may also include a transaction server (48), optionally linked to the central server (44) or to the computer network. The transaction server (48) may be associated with a third party and not with the operator of the central server (44). The transaction server (48) is operable to generate transactions including payment transactions enabling patients to purchase drugs (including for example to pay for the portion of a drug that is not covered by an insurance plan, as determined by the adjudication process controlled by the adjudication server (46)).

Figure 4:
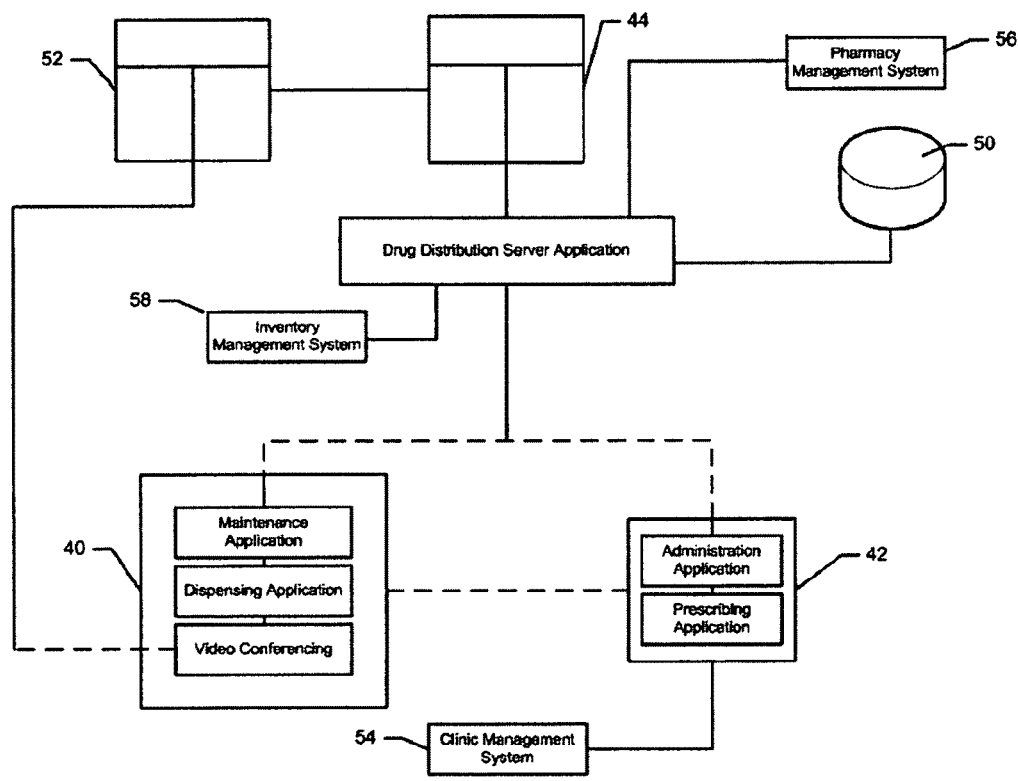
FIG. 4 is a further system diagram according to an embodiment of an aspect of the present invention.

FIG. 4 illustrates representative resources associated with the system of the present invention, and also certain additional system components that may be part of or linked to the system of the present invention.

The central server (44), in one aspect thereof, includes or is linked to a Drug Distribution Server Application (which may consist of a series of applications or an application repository) that provides access to the functions described below, including the functionality of the computers associated with the medical professionals (shown as (42) in FIG. 3) and the functionality of the dispensaries connected to the system (shown as (40) in FIG. 3). The Drug Distribution Server Application may include or be linked to a number of different computer programs or additional computer servers associated with such functionality. FIG. 4 illustrates a particular aspect of the Drug Distribution Server Application that includes or is linked to an Inventory Management System (58), further described below. In addition, the Drug Distribution Server application is linked to a Pharmacy Management System (56) for supporting the related processes described below.

Computer (42) in one aspect thereof, includes or is linked to an Administration Application and a Prescribing Application. These may consist of one or more software utilities in order to provide the functionality described below.

The Pharmacy Management System (56) should be understood as a standard software system, either custom or commercially available, that is used by a pharmacy to control patient information, scheduling, adjudication, etc., and may be linked to the Drug Distribution Server Application to track and record the prescribing and dispensing of drugs.

Dispensary (40) in one aspect thereof, includes or is linked to a Maintenance Application and a Dispensing Application.

These may also consist of one or more software utilities to provide the functionality described below.

The dispensary (40) may also optionally include or be linked to a tele conferencing or video conferencing utility for providing communication between the dispensary (40) and a remote location in order to provide, for example, video conferencing communication between a patient and a pharmacist. In one particular implementation of the present invention, the system also includes a video conferencing server (52) which is linked to the video conferencing, which elements co-operate to provide said video conferencing functionality.

System components, software components, or other utilities are discussed herein as means for illustrating the operation and implementation of the present invention. It should be understood that the present invention may not be limited to particular software, system, or network architectures or configurations, or to specific allocations of resources or functionality as between particular system components, software components, or other utilities. It should be understood that one or more system components, software components, or other utilities, could be provided as a greater or lesser number of system components, software components, or other utilities. Also, for example, a number of software components described, in particular on the computer (42) on the prescribing side, may be provided as an integrated appliance. A number of software components described could be pre-loaded on a communication device. While add-on utilities have not been discussed, it would be obvious to a person skilled in the art that various add-on utilities can be included, for example, to enable maintenance functions, reporting functions, scheduling functions, and so on. Similarly, various additional utilities or interfaces may be made part of the dispensary (40) or the computer (42) to provide enhanced features, building on what is described herein. The present invention is not limited to any particular software structure, including any modular structure.

Figure 5:
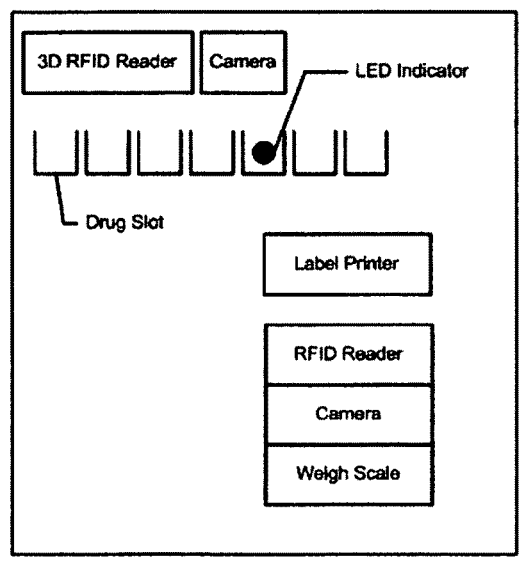
FIG. 5 illustrates a schematic of a robotic prescription dispensary.

A schematic diagram depicting elements of a robotic prescription dispensary is provided in FIG. 5. This embodiment is a robotic prescription kiosk or "dispensary". The dispensary includes drug slots for separate drugs, LED indicators for indicating the proper slot when stocking the dispensary, a label printer, preferably two RFID readers, with one of them a three-dimensional reader, internal and external cameras, and a weigh scale. The casing of the dispensary is preferably formed of steel having a nylon powder coating with sleek finish. Hardware devices should be mounted internally securely. Jacks located on the back provide for LAN, WiFi and power, for example. For the application control software, by way of example, a Microsoft WINDOWS™ based PC running custom designed application and controller software with off-the-shelf driver software can be used. There is provided a prescription bar code reader that reads standard bar codes for scripts in accordance with the present invention. According to one implementation, a 4" wide commercially available double-sided cheque scan can be used. A payment terminal will allow for various methods of payment, including debit and credit cards.

For use with the system, all credit cards or debit cards conform to the physical dimensions as specified by the ISO-1 standard size (85×54×0.8 mm). Preferably the processing will be done directly with a bank rather than through third party processing. "Track 1" and "Track 2" shall be read from the cards, and the data passed to the local server in a message bundle for processing, in a manner that is known.

For the debit cards, the keypad needs to be secure. A debit keypad can only be used in circumstances where the transaction can be monitored by a live person. If any tampering is detected, the dispensary scrubs the transaction. Preferably all pin data is in volatile memory and never stored or committed to permanent storage.

Regarding security, there will be sensors within the machine to indicate that door was opened, and all door open events will be logged. With the lock closed, the circuit is armed. Any disturbance will cause the alarm to trigger. With the lock open the circuit is disarmed, however, if there is any tampering with the inside of the delivery area, a warning will be generated. All warnings and alerts are sent to the server to notify appropriate staff.

Access to the dispensary will be granted in three separate ways:
1. An employee card is assigned a magnetic card that is an encrypted access card. If an employee uses the same employee card at different clinics while at one clinic then a cloned card is in use. This type of usage should be detected and the locking out of both cards would occur.
2. A PIN number provides access, using either the touch screen or keypad.
3. A physical key provides access, similar to other dispensaries.

The employee card and the PIN will release the electronic lock, and the physical key will release the physical lock. When the door is open with authorization, the machine enters a maintenance/admin mode which enables extra functionality that is not otherwise available, e.g.: (i) using the embedded cell-phone to call central office; and (ii) using the display and keypad for editing machine parameters and/or initiating communications with the central server (44).

If unauthorized access if detected, a small concealable wireless camera will begin recording. There should be source of illumination when the door is opened sufficient to light up the face of an intruder. One option (for streaming video or photos) is to use a wireless system based on 802.11, for example, such that the camera is essentially a peripheral of the local server. An 802.11 repeater may be needed. All wireless components should be limited to known MAC addresses and encrypted traffic. Another option (for photos only) is to use a camera tied to the customer support cell phone (no 802.11 required).

Once the drug inventory hits a predetermined low water mark and/or a periodic milestone is achieved, depending on the inventory management approach described below, a purchase order type message is sent from dispensary to the central server (44). This message can tell the serviced provider what drugs the dispensary needs. All other pending service requests will be scheduled at the same time to ensure that a service trip is optimized.

When the lockbox is full or nearly full, the entire lockbox is replaced with an empty one, and the full one is taken away by the service provider. When the lockbox is opened the prescriptions should be audited and confirmed that all prescriptions retained by the dispensary matches the prescriptions audited.

Regardless of capacity of the rejects bin, rejected drugs should be collected as soon as possible after being detected (and replacement stock put back in the machine).

There should be regular maintenance and top-up of consumables (media & ink) for all printers involved.

A drug delivery hopper is ideally provided at a reasonable height to allow access for most users. Preferably there is a light inside. An RFID reader can be placed in the hopper determines if a product is not picked up by a user. A camera also takes a picture of the item, and can be viewed in real-time by the call centre pharmacist. The hopper is also subject to a lock, controllable from the PC, and that is tamper resistant and sturdy.

If the RFID read of a bottle does not equal the prescribed drug, then the drug goes to a waste bin for collection by servicing. The dispensary software will automatically issue the error to the call centre, and will decide to lock machine and/or take over session and speak to consumer.

It is generally required that the drug information printer print the drug information sheet from the adjudication database; and that the printer itself be sturdy, and notify the PC of ink status, jam and paper out conditions required. The printer is preferably mounted securely, and has a relatively large paper capacity (e.g., at least 500 sheets).

A 15" or 17" touch screen is provided, for example, for the input, allowing a large text size and potential advertising space. A keyboard is also provided with a trackball for further input.

A camera is provided for security and for call centre interaction. Similarly, an internet-protocol phone is provided for call centre interaction, facilitating the system for blind patients. Alternatively, a speech output device may be implemented for instructing the patients via computer generated voice.

An uninterruptible power supply (or "UPS") provides for a graceful shutdown in the event of a power failure (once a transaction is completed).

A wireless LAN adapter is preferably provided to connect to the doctor's handheld and maybe office LAN. Cable connectors on the back of the machine include the power cord for the unit (e.g., need one cord out from UPS and internal power bar or UPS multiple plugs). A network cable female jack is provided connecting to high speed Internet service. A network cable female jack is provided for LAN connection to the doctor's office, or handheld etc. Further, a male coaxial cable jack is provided for an antenna for WiFi transceiver.

The dispensary may optionally incorporate biometrics technology for authenticating the identity of a user of the dispensary.

The patient typically interacts with the dispensary via a standard input device such as a touch screen monitor or keyboard and trackball. In one particular implementation, the patient selects from a number of options using a touch screen monitor. The options presented are "New PharmaTrust Prescription", "Pick-up Refill" and "New Handwritten Prescription". Upon selecting New PharmaTrust Prescription, the patient is prompted to insert the prescription printout that was provided by the doctor.

Figure 6:
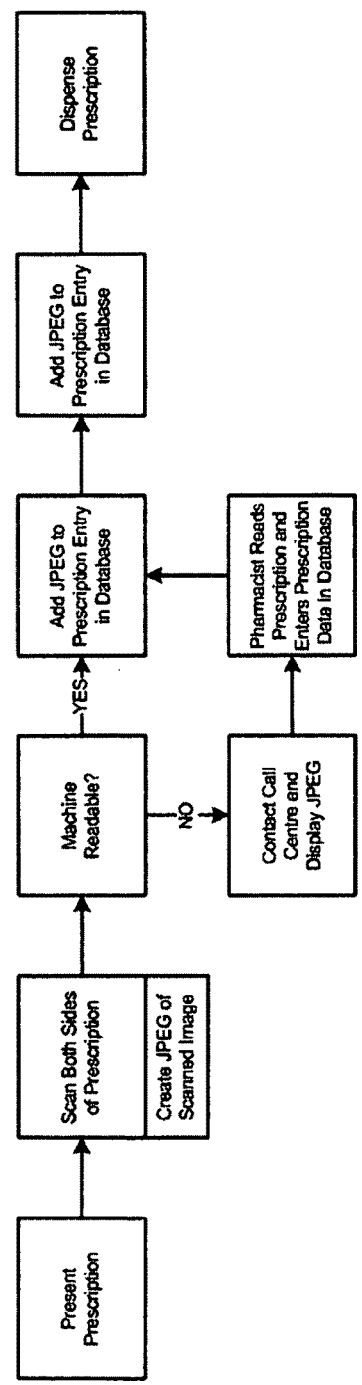
FIG. 6 is a flowchart illustrating steps for having a prescription filled.

The method steps for having a prescription filled are illustrated in FIG. 6.

Once the patient has inserted the script or prescription printout, both sides of the printout are scanned, and the barcode is read to enable the dispensary to identify the prescription in question. Ideally, a mechanism for scanning both sides of a printed or handwritten prescription is implemented for flexibility. In another implementation, the RFID of the prescription or chit would be read to identify the prescription. In yet another implementation of the invention, the patient's identification number (health card, account number, etc.) would be used for identification of the patient and prescription to fill.

The image of the script is scanned to determine if there is no bar code. If it is machine readable, the dispensary via the central server pulls up the prescription entry in the database. If the script is only human readable, a validation agent such as a pharmacist at a call centre is contacted and provided with the scanned image of the script, enabling the agent to manually retrieve the prescription entry in the database. Depending on the jurisdiction, it may be advisable to have a validation agent review and approve all prescription requests provided to a dispensary.

The system preferably requests confirmation of the patient name. Typically, the patient is also prompted to accept the dispensary terms of use at this time. The patient clicks a button on the screen to confirm, or a cancel button to terminate the transaction, and retrieve their prescription.

The dispensary then displays a list of the drug to be dispensed. Typically, the patient can deselect any items they do want dispensed at the present time (e.g., maintenance drug they already have on hand or at home). These items can be saved for later pick up, or delivered at a later time via a home delivery service. The patient presses an on-screen button to confirm. In the same way, the patient confirms their contact information. If changes are required to the mailing or billing address, the patient can make them using either an integrated or on-screen keyboard. The mailing address can be used for any repeats or other items to be sent via a home delivery service.

According to a particular aspect of the present invention, it should be understood that the present invention enables a substantially automated prescription repeat service that can be offered through home delivery, as an example. This is provided, for example, by integrating the described system with a system used by a home delivery service to process repeat prescriptions of drugs. Repeats can also be filled at the robotic prescription dispensary In an implementation including adjudication of benefits coverage, the patient is asked to confirm or enter their drug benefits coverage information. Typically, this information is edited in the same manner as address information.

In implementations of the invention that include pharmacist consultation or intervention, once all patient information has been confirmed, a video conference call with a call centre pharmacist (typically an aspect of the services delivered by a service provider who is responsible for managing patient interactions) is initiated. In addition, the patient generally has the option to communicate with a call centre pharmacist at any time. This is initiated by pressing a "Call Pharmacist" button generally provided as a persistent button on the dispensary user interface.

Note that although a "pharmacist" is discussed herein as the validation agent in most cases, it should be understood that the present invention is not necessarily limited to a validation means for a human readable script involving a pharmacist per se, but can be any person who is capable of dispensing drugs to a patient, depending on the regulatory rules of the particular jurisdiction.

By whatever means and at whatever point the video conference is initiated, it is generally facilitated via standard video conferencing systems over the Internet, for example, via a secure channel such as a VPN (Virtual Private Network). The dispensary generally has multiple video cameras in place to enable the pharmacist to see the patient and the drug (while it is still within the dispensary) simultaneously. A standard web cam is used to provide a live on-screen view of the pharmacist for the patient. In one implementation, the pharmacist's image is displayed on the same screen as the other interactive components of the dispensary user interface. An alternative implementation uses separate computer displays for the graphic user interface and the video conference display. Voice conferencing can be accomplished via a standard microphone and speaker embedded in the dispensary, or, to support patient privacy, a standard telephone handset connected to the dispensary. Voice data is generally transmitted via the same system as the video conferencing leveraging the same communication system (e.g., Voice Over IP).

The pharmacist is provided with a proprietary software application that enables them to review all relevant patient and prescription information and remotely control the dispensary. This control enables the pharmacist to add or edit data (e.g., patient information, SIG, etc.) and authorize or terminate the dispensing of drug to the patient. The information presented to the pharmacist includes:

All information contained on the prescription.

All pedigree information associated with each drug item before it is dispensed; this information is drawn from the data associated with the given item's RFID, and is used for comparison before releasing the drug o the patient (see below).

A standard adjudication system, typically a third-party system linked via API (Application Programming Interface) or a simple data connection to the system. This application is used to process drug benefits claims through the standard systems in use within the jurisdiction.

The dispensary control interface that is used to add or edit information and control the dispensing process.

Live video stream of the patient.

Live video of the patient bay (inside the dispensary), which is used for visual inspection of the item to be dispensed before it is released to the patient.

In transactions where the patient has received handwritten prescription or a prescription printed using a system that does not create a unique ID for use with the dispensary (i.e. a barcode, RFID or otherwise corresponding to a unique prescription entry in the system), the patient would select "New Handwritten Prescription" on the dispensary touch screen to begin the transaction. Similar to the process outlined above for PharmaTrust prescriptions, the dispensary would scan both sides of the prescription. As the prescription information would not be present in the system, a video conference call with a call centre pharmacist would be initiated directly following the prescription scanning process. The call centre pharmacist uses that same systems outlined above, and is presented with the same information and authorization displays as described for a PharmaTrust prescription, however, they would manually enter all patient and prescription information (unless the patient already exists in the system, is which case they would simply need to add the prescription information to create a new prescription in the system). In this case, the image of the scanned prescription is very important, as it is used by the pharmacist to visually authenticate the prescription as is currently done in pharmacy, but from a remote location.

Once the video conference has been initiated, and all require information has been entered, the drug benefits claim is submitted for adjudication using whatever standard system is customary in the jurisdiction. For example, the pharmacist can use a standard pharmacy management system to submit the claim based on information manually entered into the system or automatically transmitted to the pharmacy management system by the system. In one implementation of the invention, this data transmission is accomplished via an API provided by the pharmacy management system software vendor. In other implementation, the transmission could be facilitated via posting data from the system to the pharmacy management system at the database level, or any other appropriate data sharing method. In submitting a benefits claim, pharmacy management systems typically use either private networks or secure Internet connections to communicate with benefits providers using messaging protocols standardized by benefits providers or regulatory bodies. These messaging standards can also be leveraged by the dispensary system for automated submissions with no pharmacist intervention, or pharmacist-assisted submissions without the use of a third-party pharmacy management system.

Once a claim has been submitted, the benefits provider generally responds in near real time in a meaningful way according to the jurisdiction's messaging standards. The response will indicate whether the payment for drug is covered under the patient's benefits plan, and how much the co-pay (the amount the patient is required to pay out of packet, if any) is. This information is either passed automatically to the dispensary system, or manually entered into the dispensary control screen by the pharmacist.

At this time, the results of the benefits claim are typically displayed to the patient via the dispensary display screen.

If the drug was not covered by the patient's benefits plan or the patient is required to pay a co-pay, the total payment required (which will generally include a professional services fee similar to the dispensing fee charged by pharmacies) is displayed. The patient chooses their preferred method of payment. Most implementations allow payment via debit or credit card, while others include the ability to pay via cash using integrated standard dispensary cash box systems. Credit and debit card payments are typically facilitated via integrated mag stripe readers, secure PIN pad hardware appropriate for use in unattended dispensary settings, and software/system connection with credit/debit card processors. Connection to card processors are typically implemented using private networks, wireless connections or secure Internet connections to send and receive processing messages via an API or other such interface provided by the card processor.

Upon approval of the payment transaction, the drug is picked, labelled validated and presented to the patient along with any required drug information and/or receipts. In a particular implementation of the invention involving a remote robotic prescription dispensary, this process is accomplished without the physical intervention of the pharmacist or any other administrative staff. The dispensary is comprised of a certain number of drug shelves, based on the requirements of the clinic in question. Ideally, each dispensary will be configured to provide the most efficient use of space and optimize inventory availability. The inventory management system developed is designed specifically to provide optimal customization of slot sizes and drug inventory based on the prescribing history of the clinic in question. In this implementation, the dispensary has a robotic pick head that is used to retrieve the standard dosage drug items from the slot in which they are stored. To dispense a given item, the pick head moves to the appropriate slot, and retrieves the desired item ideally using an apparatus designed to handle items with differing shapes, sizes, weights and forms (e.g., large and small boxes, bottles, etc.). Once the pick head has retrieved the item, it will move the item to an appropriate location for scanning of the item's RFID tag. Ideally, the RFID scanner would be capable of detecting the presence of multiple RFID tags to ensure that the wrong item is not mistakenly dispensed to the patient. It is important to note that the system has access to the stocking matrix of the dispensary (i.e. which items are assigned to which slots), and as such can determine if the correct item has been selected by comparing the RFID tag scanned with the expectation based on the stocking matrix.

If the RFID scan fails for whatever reason (e.g., missing or incorrect tag, multiple tags, etc.), the item is moved to the discard bin for later removal during the normal inventory management and dispensary maintenance process as described herein.

A successful RFID match will cause the item to be moved to the labelling station of the dispensary. This movement is generally performed by a robotic arm or other such mechanism. A label for the item is printed with all information required by regulations in the jurisdiction. This information typically includes patient name; doctor name; patient address; drug name and manufacturer; drug quantity, form and formulation; number of repeats; SIG (patient instructions for taking the drug); clinic contact information; etc. In one implementation, the drug label is printed on a 2"×3" label that includes branding associated with the clinic and dispensing service. Once printed, the label is applied to the drug item in such a way that it cannot be easily removed. This is done to support patient safety by helping to ensure that the appropriate drug information is available on the drug package. The label should ideally be applied in a manner that can reliably apply the label securely on various package sizes, shapes and materials with appropriate placement on all packages in use (i.e. the label should be securely applied with straight positioning on all items dispensed via the dispensary).

Once the drug item is labelled, it is generally moved to a patient bay (a location where it can be retrieved by the patient) via a conveyor belt or other such mechanism. In one implementation involving pharmacist-assisted remote dispensing, the patient bay includes a camera that is use to provide the pharmacists a real time video feed of the drug before it is released to the patient.

Before the item is released to the patient, it undergoes a final set of validation checks to protect patient safety and ensure that the correct item is being dispensed. In one implementation of the invention all pedigree data associated with the item (during the process of preparing the item for use in a dispensary) is compared with the attributes of the item in the patient bay. An RFID scan is performed to ensure that the item is the item scanned earlier in the process. The item pedigree attributes are analyzed to ensure that the drug is safe to dispense. For example, the expiry date has not passed, there has been nor recall on the item's bin or lot by the manufacturer, etc. The item's environmental variable history is processed to ensure that it has been subjected to no unacceptable excursions in temperature or humidity. This is supported by the fact that temperature and humidity are continually monitored and logged in the warehouse as well as the dispensary. By examining the environmental variable log for the times in which a given item resided in the warehouse or a particular dispensary, temperature and humidity history can be determined for the item and compared with the acceptable ranges as set by the pharmaceutical manufacturer. The package history of the item is also drawn from the event log of the system, and validated for acceptability. This history is comprised of each movement-based event to which the item has been subjected. For example, the history could log the date and time of shipment from the manufacturer, receipt in the warehouse, repackaging and serialization (i.e. application of the item's RFID tag and entry of its pedigree attribute in the inventory management system), placement in dispensary and dispensing to the patient (the current date and time). The presence of all of these events in the item's history provides a strong indication that the appropriate processes were followed, and delivers further evidence in support of the safety of the drug for dispensing to the patient. A weigh scale is also present in or near the patient bay, and the item weight is compared to the weight in its associated pedigree data set to make sure that it is within an expected tolerance based on the addition of the label, etc.

It should be understood that this set of validation data and checks provides the necessary assurance prior to releasing the drug to the patient of the item's identity (i.e. the item in the patient bay is what it is supposed to be) and suitability for patient use. These checks provide a much higher standard of patient safety and drug tracking than is available with existing systems, which track none of the items listed above in a reliable or auditable manner.

In implementations involving automated dispensaries with no pharmacist involvement, the camera in the patient bay is used to take a digital picture of the item before it is dispensed. This picture is added to the item's history, and used for audit and/or tracking purposes.

In implementations in which dispensing is pharmacist assisted, the image of the item in the patient bay can be compared by the pharmacist to the image of the item taken when it was initially RFID tagged and entered in the system (i.e. serialized) and stored with its pedigree data. This final visual inspection, coupled with the checks outlined above, provides an even higher level of safety to the dispensing process. In these cases, the pharmacist can choose to discard the item if any of the checks fail, or the item does not pass their visual inspection. Otherwise, they can approve the dispense, and release the drug to the patient. At this point a digital image of the item is taken and saved in its history as described above.

As with other types of vending machines, the drug is typically released to the patient by opening the external door to the patient bay. The patient can then retrieve the drug. Sensors (e.g., light beam or any other appropriate mechanism) are used to determine whether the item is retrieved by the patient. Typically, after a certain amount of time, the patient is prompted on the dispensary graphic interface display to determine if more time is required to retrieve the item. If the item is not retrieved, the door to the patient bay will close and lock, and the item will be moved to the discard bin. In this case, the failed dispense is logged, and the call centre is notified and prompted to take appropriate action, and the transaction is terminated. Once the transaction has been terminated, the dispensary returns to the welcome screen, and resumes its normal operating behaviour.

If the item is retrieved by the patient, the door to the patient bay closes, and the process is either repeated (starting with picking the next item from the appropriate shelf) for the next item, or if all items have been dispensed, the transaction is completed.

According to a further aspect of the present invention, drug information sheets, payment receipts and Drug Pedigree Certificates can be printed for the patient at the time of the transaction. An example of a Drug Pedigree Certificate is provided as FIG. 7. Printing of drug information sheets and Drug Pedigree Certificates is generally performed as a parallel process upon the release of each item to the patient. Payment receipts are typically printed following the release of the final drug item.

In pharmacist-assisted implementations, once the transaction has been completed, the pharmacist terminates the video conference with the patient.

In situations involving a single doctor or small office, an alternative implementation of the invention is possible. Rather than use a robotic dispensary as outlined above, a smaller unit that includes the patient interface elements of the dispensary (i.e. prescription scanner, display, payment mechanisms, dispensing software, etc.) can be put in place. In this case, all of the processes outlined above would be carried out in a manner similar to the processes described for a typical dispensary, with the exception of the processes associated with picking, validating and releasing the drug item. In such an implementation, once the payment transaction has been completed, the patient is presented with a chit (e.g., a token, RFID tagged card, mag-striped card such as those used in parking garages, etc.) to be presented to the receptionist or other designated individual. The receptionist would log into a dispensing console (ideally a standard computer with any required peripherals such as an RFID or barcode scanner, information sheet printer, etc.), scan the chit, and be presented with information on which items are to be dispensed. The drug packages could reside in a secure locked cabinet of an appropriate sort. The receptionist would unlock and open the cabinet, and retrieve the required drug items. Each item would be RFID scanned into the dispensing console system for validation of the pedigree attributes described in the processes above. A weigh scale could also be connected to the console to provide weight comparison as described above. Upon validation of the item to be dispensed, the receptionist would print the drug information sheets, Drug Pedigree Certificates and receipt, ideally on a standard high-quality printer, and give the drug items and printouts to the patient. In this manner, the cost and space requirements for a dispensary can be mitigated to deliver a viable system for small doctor offices. At the same time, the patient will still receive the safety and tracking benefits offered by the system.

Once an item (or items) is dispensed to a given patient, the patient's medical file is typically updated on the database, and any repeats on the prescription are saved in the system. Generally, these repeats are transferred to whatever pharmacy management system is in use by the service provider via the same API or data-sharing connections used for benefits claims.

By updating the patient file, the doctor can be notified that the patient has filled their prescription. This is information that doctors do not receive under the currently prevailing system for filling prescriptions. In a particular implementation of the invention, the doctor is also provided a repeat approval function within the prescribing application. This function displays all of the repeats that will be required in the near future by patients who elected to fill their prescriptions at the dispensary (or who have had their repeat transferred to the service provider's pharmacy from another pharmacy). The doctor selects repeats for approval based on the on-going need of the patient. In this way, patient safety is supported by more focused drug regimens, and doctors remain involved in the on-going supervision of patient drug between office visits. The healthcare system is also spared the additional cost of filling prescriptions for which the doctor has determined there is no further need. Typically, once the doctor has approved a given repeat, payment is processed via a pre-authorized credit card transaction or other appropriate method, and the drug is either delivered to the patient by a home delivery service (courier or otherwise) or can be picked-up by the patient at the dispensary.

To pick-up a pre-authorized refill from the dispensary, the patient will typically press a "Pick-up Repeat" button on the graphic display of the dispensary, and be either immediately connected with a call centre pharmacist (as with handwritten prescriptions described above) or enter an authorization code provided by the service provider. The authorization code could be anything from patient account login information to a mag-striped patient card issued by the service provider. In any case the authentication method would provide assurance to the identity of the patient in question. Once the patient has been identified, the transaction would take place in much the same manner as for a new PharmaTrust prescription.

Figure 8:
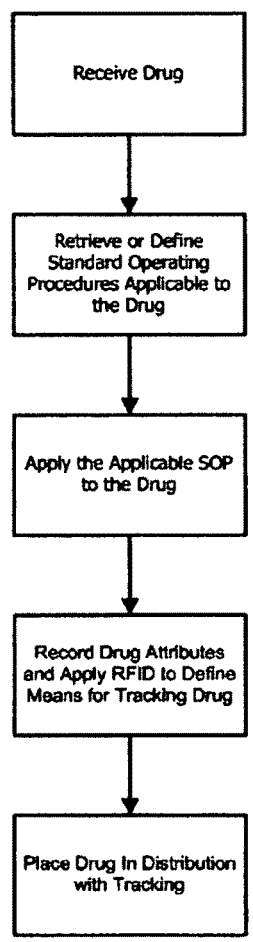
FIG. 8 is a flowchart illustrating steps for a method of drug distribution.

With reference to FIG. 8, a drug distribution method is a further aspect of the present invention. In accordance with this aspect, product is received from a manufacturer or supplier and when it arrives at the warehouse for stockpiling it is compared against orders placed in the system. If the product matches that which has been ordered, it is queued for inspection by Quality Assurance. A set of Standard Operating Procedures (SOP) is pre-defined for the handling, preparation, tracking and distribution of any particular drug, and they apply throughout the distribution channel, from receipt of the drug at a warehouse to dispensing the drug to a patient. These procedures provide detailed workflow and end product packaging instructions, along with details on how to handle any exception cases that may be encountered. This can be important for quality control purposes. The initial product inspection is carried out as per the appropriate SOP. Rejected product is handled as indicated in the appropriate SOP. Approved product is resealed in its shipping container, and entered in the warehouse inventory system.

An RFID tag is applied to the shipping container. The RFID tag is then scanned into the inventory tracking system.

Typically, the inventory tracking system is a custom developed system designed to track items through the various forms and status conditions through which they pass in the processes associated with the invention. This must include states such as bulk inventory items (i.e. items in no-standard dosage packaging) as well as standard dosage items fully prepared for use in a dispensary. It must also track the differing possible states and locations for each item such as queued in the pick shelf, assigned to a given dispensary, or at rest in a dispensary. In addition, the inventory tracking system must have the capability to track all required pedigree attributes and data used throughout the system. Pedigree attributes are those attributes of an item that impact its suitability for use by patients, but remain largely static throughout its life cycle. As an example, the following pedigree attributes are used within one implementation of the invention:

Drug Name
    Drug Manufacturer
    DIN Number
    Lot Number
    Bin Number
    UPC Code
    Expiry Date
    Date of Receipt by the Service Provider
    Purchase Order Number (PO Number)
    Item Weight
    A Digital Picture of the Item taken when it is first "serialized" (i.e. has the RFID applied, pedigree attributes logged, and is prepared in standard dosage form)

Another set of data is generally tracked for each item, this data set being called "pedigree data". Pedigree data can be a set of data representing any non-static events that may impact the suitability of a standard dosage item. This data is generally tracked as an event log. Examples of information tracked in this data set are:

Environmental Variables:
        Temperature
        Humidity
    Transportation Events:
        Date Received from Manufacturer
        Date the Item is Serialized
        Date of Shipping to a Dispensary
        Date the Item is Dispensed to the Patient, etc.

The nature of this information enables strong tracking of an item throughout its life cycle, and provides strong assurance of its suitability for use by patients.

The container is staged (i.e. place in an appropriate designated area) for unpacking and processing as per the appropriate SOP.

The system is based on the concept of standard dosage dispensing. In this type of dispensing, single unit items are referred to as "standard dosage" items or packages. This is to indicate that the items are appropriate for use in the dispensary and for dispensing to patients. The actual number of pills, capsules, etc. contained in a given standard dosage package will vary based on the drug and dosing regimen. This regimen is derived from information provided by the drug manufacturer, and the common dosing practices for the drug in question. By standardizing the dosing process, patient safety is support through more predictable drug usage and compliance with manufacturer recommendations. It is possible that a single drug type may have multiple types of standard dosage packages (e.g., one-month and three-month supplies).

The multi-unit shipping containers are retrieved for unpacking as required based on an inventory queuing report produced via the inventory management system (58) to detail which drug product has been received and must be prepared in standard dosage packaging.

The RFID of an appropriate container is scanned into the inventory management system (58) to indicate the drug to be prepared as well as its various attributes. The container is then opened, and the single unit items are handled as follows:

Items that are appropriate for use in a dispensary are prepared for processing as detailed herein.

Items that are not appropriate for use in a dispensary are queued for repacking into appropriate dosage and form as detailed herein.

Note that the attributes drawn from the RFID scan will be applied to each of the standard dosage items drawn from the container.

Once the standard dosage items have been queued for processing, a unique RFID tag is placed on each package as per the appropriate SOP. The attributes of the drug drawn from its parent container are also associated with the standard dosage item in the inventory management system. Pedigree attributes specific to the individual item are then added to its profile. These attributes are used for identification and tracking processes throughout the system. Once the items have been added to the system, they are placed in a pick shelf to be retrieved during the dispensary inventory replenishment process.

The pick shelf houses a number of bins that are used to stage items that have been prepared for use in a robotic prescription dispensary. Each bin on the pick shelf has a bar code or RFID for easy location and identification, and contains only a single drug type, form and package. When placing a standard dosage item into the bin, the item's RFID is scanned into the inventory management system (58), followed by scanning of the bin's RFID or barcode. If the drug type, form or package does not match that assigned to the bin, the user is notified, and prompted to select a different bin. If the drug type, form and package matches that assigned to the bin, the user places the item in the bin and repeats the process with the remaining items to be placed in the pick shelf. The inventory management system (58) maintains an on-going inventory of all items that have been placed in the pick shelf.

When an item must be repacked for use in a dispensary, the container RFID is scanned into the system to indicate the drug to be prepared as well as its various attributes. The drug is removed from the manufacturer packaging or selected from bulk packaging (whichever is appropriate), and prepared for repacking as per the appropriate SOP. The drug is counted in standard-dosage quantities, and repackaged into dispensary-appropriate packages as per the appropriate SOP. Drug labels are printed and applied to the standard dosage packing. These labels may include all information (e.g., manufacturer name, drug name, formulation, drug form, quantity, expiration date, lot number, etc.) legally required for prescription drug. This information is determined via the product association as indicated by the RFID scan described above. The completed standard dosage packages are compared against the Item Masters as per the appropriate SOP.

In one implementation of the invention, dispensary inventory is restocked by first producing and reviewing a clinic inventory report via the inventory management system. This report displays the stocking requirements for any or all dispensaries. Stocking requirements are generally based on the prescribing habits of the clinic combined with the actual historic inventory flow through the dispensary.

The inventory management system (58) is then used to select a particular dispensary requiring restocking. A visual representation of the dispensary and the arrangement of its internal drug shelves (along with drug type assignments for each slot and detail of the current inventory level of each slot) is displayed on the inventory management system (58) computer screen. Using the inventory management system (58), a required item is then selected from the pick shelf, and is RFID scanned. Upon scanning, it is automatically assigned to an appropriate slot in the dispensary. This process is repeated for each required item. In this way, each item can be assigned to a particular slot before it is delivered to the clinic is question when desirable for the implementation of the invention.

Referring to back to FIG. 4, the inventory management system (58) can be a standard, commercially-available software program or custom designed and is linked to the Drug Distribution Server Application associated with the central server (44). The inventory management system (58) enables tracking of movement of the drugs between the warehouse and the dispensaries, and implements rules established by the SOP, and may comprise additional functionality such as trend spotting to predict inventory demands and reporting. For example, the inventory management system (58) can ensure transport of drugs between one or more warehouses and dispensaries, optimizing efficiency while at the same time conforming to SOP for a particular drug, e.g., to ensure delivery within reasonable time based on a drug's shelf life.

A clinic distribution container is then selected for use. These containers are used to transport drug items to dispensaries, and will contain only those items required for a particular dispensary to simplify the distribution and dispensary loading process. In addition, each container is sealed for security before it is transported to the dispensary in question.

All items assigned to the particular dispensary are placed in the distribution container. An RFID tag is placed on the container, and scanned into the inventory management system (58), which assigns the container to the dispensary in question. The distribution container is then staged for pickup by delivery personnel.

When delivering product to dispensaries residing at clinic locations, a clinic delivery report is produced and reviewed via the inventory management system (58). This report displays the details of the deliveries that have bee queued as described above. Multiple deliveries may be assigned to a single "run". The appropriate delivery container is selected from the staging area. The user logs into the delivery management screen (via the inventory management system (58)). The RFID of the distribution container is scanned, and thus checked out for delivery by the user. The distribution containers are loaded into a delivery vehicle. The distribution container(s) are then transported to the appropriate clinic(s).

The following is an example of the process of loading a dispensary and removing items that have been discarded (for various possible reasons) during the operation of the dispensary.

The maintenance technician unlocks and opens the dispensary. Once opened, the dispensary enters a maintenance mode which enables the use of the internal maintenance application via a computer touch screen that generally resides inside the dispensary. From this touch screen, the technician logs into the maintenance application. User authentication can be performed via user name and password, RFID scan of the technician badge, or in another appropriate manner.

The technician scans the RFID of the distribution package to identify the items to be stocked using an RFID scanner also in place within the dispensary. The seal of the distribution container is then broken, and the container is opened.

A standard dosage item is selected from the distribution container, and placed near the RFID scanner (located inside the dispensary). The item's RFID is automatically scanned by the maintenance application. The maintenance application indicates the appropriate slot location for the scanned item within an inventory matrix screen (the same visual representation of the dispensary shelf layout described above), and an LED or other visual indicator lights up in the slot within the dispensary. The indicated slot is that to which the item was assigned in the processes described above. The technician places the item in the slot indicated. The technician confirms that the item has been placed by clicking a button in the maintenance application. This process is repeated for all items assigned to the dispensary in question.

The maintenance technician then views a report of the items to be removed from the dispensary. This report can be run from the inventory management system (58) before the technician leaves the warehouse, or can be run from the dispensary maintenance application. The report indicates items that are known to have been discarded by the dispensary during its operation. All items are removed from the discard bin in the dispensary, and the technician checks for additional items that may have fallen into other areas of the dispensary. All recovered items are placed into the distribution container that was used to transport items to the dispensary. The distribution container is then closed and sealed for return to the warehouse, and the technician logs out of the maintenance application. The technician closes and locks the dispensary, which returns the dispensary to its normal operating status. The distribution container(s) are loaded into a vehicle and returned to the warehouse.

Once the containers are transported to the warehouse, the returned distribution container is unloaded from the delivery vehicle. The inventory management system is used to log the return of the distribution container via an RFID scan. The seal on the container is broken, and the container is opened. Each item is inspected by quality control as per the appropriate SOP. Rejected items are disposed of as per the appropriate SOP. All patient identifying materials are removed from each item, and queued for disposal. Items approved for use are prepared for re-entry into normal stock as per the appropriate SOP. These are treated in the same manner as normal incoming stock (described above). Inventory is adjusted to reflect the stocking decisions made during this stage (i.e. the fate of each item is updated in the inventory system). All patient-identifying materials are disposed of as per the appropriate SOP. All RFID tags used in this process are disposed of.

It should be understood that the data and inventory management processes, detailed event logs and use of tracking mechanisms such as RFID, etc., leveraged throughout the system deliver highly detailed auditing capabilities that can be used to delivery accuracy in dispensing and promote patient safety.

Generally, every system event in each element of the system (e.g., inventory management system, dispensary applications, robotic controls, environmental data, etc.) is logged for audit and/or comparison purposes. Feedback from software application as well as hardware systems are logged centrally, and can be used in the process of safety audits, error identification and handling, system performance tuning, examination of trends, etc.

Figure 7:
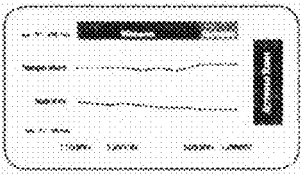
FIG. 7 illustrates an example of a drug pedigree certificate in accordance with an aspect of the present invention.

One significant application of this auditing is demonstrated by the production of the Drug Pedigree Certificate (as shown in FIG. 7).

This certificate provides a visual reference supporting the suitability of a given standard packaged drug for use by the patient. The data used to produce this certificate is a combination of the pedigree attributes and pedigree data (described elsewhere is this document). The data elements are evaluated in manners appropriate to the given element.

For Example:

Evaluate the current validity of certain data elements (e.g., ensure the expiry date has not passed).

Comparing certain data elements against data provided by manufacturers (e.g., ensure that no recall has been placed against the lot or bin number of the drug).

Measure certain data logs against manufacturer data (e.g. read the temperature and humidity log data of the warehouse and dispensary for the time frames during which a given item resided in the location, and compare to the acceptable range for the drug to ensure that the has not been subject to any unacceptable excursions in environment variables).

Compare certain current data elements to those logged at the time an item was initially serialized (e.g. visually compare the digital image of the item in the patient bay with the image taken at the time of serialization to ensure that it is the same item, or compare the weight of the item at the time of serialization and dispensing to ensure that it is within a set tolerance range).

The combination of these analyses and data checks provides a very high level of assurance to the suitability of the drug for use by the patient.

As discussed above, the present invention is a robotic based prescription dispensing system designed preferably for a doctor's clinic operation. The system dispenses medicine immediately, conveniently, more accurately and at less cost than traditional drug store based dispensing systems.

Conceptually, the present invention operates as follows: a patient is in the examination room with their doctor. The doctor has reached his/her diagnosis and is in the process of writing a prescription using a computer-implemented device, such as a tablet computer. The prescription interface may notify the doctor and patient of the drug plan coverage allowing the doctor and patient to make the best decision for the drug they need. When the drug is selected, a drug utilization review can be conducted to ensure check drug interactions. The prescription along with drug education material is then printed.

The patient then walks to a system unit in the waiting room and inserts the prescription. Within minutes, the machine selects the appropriate pre-packaged drug, scans it for verification, and releases it to the patient. The process is painless when compared with the prospect of patients having to travel to fill a prescription. More importantly, the patient's medical record is updated with the record of the dispensing and the patient now is taking their meds immediately, getting better faster. If this is a maintenance drug, the prescription repeat will be delivered to the patient's door within days before their current prescription ends, or the patient can pick up refills at the dispensary. This seamless integration with mail order delivery improves the chances that patients will continue to take drug as prescribed because the requirement to go to a pharmacy to renew prescription results notoriously in gaps in drug treatments.

Preferably, a service provider attends to all aspects of dispensing operations. In this regard, the system of the present invention is preferably designed as a "turn key" operation for primary care clinics such that all the doctor has to do is write the prescription on the ordering tablet. Everything from the installation of the system to its daily maintenance, payment collections and accounting, health benefit adjudication, and inventory logistics and replenishment is preferably operated by the service provider.

It is known that up to sixty per cent of the prescription market is for maintenance drugs. Be it for high blood pressure, high cholesterol, diabetes, depression, etc., patient drug programs require compliance and adherence to prescribed drugs in order to maintain good health. Typically, when a patient receives a prescription and goes to a drug store for dispensing, the repeats are captured by the drug store and it is very difficult to redirect the repeats to mail order delivery. However, a system according to the present invention effectively captures and diverts prescription repeats for maintenance drugs to a home delivery service. In this regard, a service provider will operate a home delivery pharmacy for two purposes: (i) to repackage bulk drugs into standard prescription doses for the dispensing system inventory; and (ii) to offer mail order delivery services so that patients will be offered the convenience of home delivery with the service provider retaining this important revenue stream. The mail-order pharmacy and home delivery service is significantly less costly than pharmacy-based operations and takes advantage of the automation prescription drugs for order fulfillment.

Further, it is known that an average doctor writes approximately 10,000 prescriptions per year. This corresponds to enormous revenue generated for pharmacies. The present invention is designed to dispense medicine inside doctor clinics or directly to patients' home, delivering a more convenient service to patients while capturing a portion of the revenue stream that would otherwise go to pharmacies. Where appropriate, pharmacies can be given access to some or all aspects of the system, for example, in order to facilitate the choice of the patient or other situations where it is desirable for the patient to have the prescription filled by the pharmacy. Either way, however, the dispensing of drugs by doctors enables redirecting of certain revenue to doctors which in turns relieves pressure on the health care system and enables doctors to take the time required to cover drug related issues such as interactions more exhaustively and using better tools than what is currently possible under the existing system. The doctor is the entry point for patients to a drug therapy regime, yet the pharmacies have the tools, information and time to cover important health related aspects thereof. The medical details of a drug therapy regime are in the current system not fully passed on from doctor to pharmacists, which results in many cases in a loss of efficacy in the therapeutic effect, inefficiencies, miscommunication, the need for pharmacists to follow up, inconsistent instructions and so on. The present invention enables doctors to be given with better tools to manage drug treatments resulting in a more seamless healthcare system and better healthcare for patients.

It is also known that doctors routinely prescribe on average only 16-18 drugs for their patients. The present invention is designed to service a doctor's prescribing routine and cover a majority of their particular dispensing requirements.

Primary care doctors and related secondary healthcare services are increasingly organized in medical buildings that are designed specifically to address the multi-faceted needs of a divergent patient population. However, the most under-invested sector of healthcare for communications and information technology (CIT) is the primary care doctor's office. The reason for this is that for the doctor CIT has not offered sufficient tangible benefits to make the investment worthwhile. Furthermore many doctors' offices do not attain the scale of organization to make a significant CIT investment a priority or justify the staff required to support CIT operations. This technology investment can be leveraged to improve healthcare with the doctor's office as the point of contact, e.g. by delivering multimedia information on medical treatments, accessing rich content from databases, mining prescription information based on up to date information regarding drug interactions etc.

The present invention addresses this in the following ways:
1. The system of the present invention is delivered as a turn key solution with no up-front investment required by the doctor.
2. The system of the present invention offers an incremental revenue stream that provides sufficient incentive for the doctor to adopt the technologies.
3. The system of the present invention aggregates doctor practices to the scale required to generate appropriate returns on CIT investment.
4. The system of the present invention delivers the organizational ability to make a CIT investment mutually beneficial for the doctors and the patients.
5. All CIT support functions are operated by a service provider eliminating any impact on doctor or clinic operations and overhead.

The system of the present invention also addresses accuracy and efficiency issues common with pharmacy-based dispensing. Currently, most prescriptions are paper-based. This results in up to 10% of prescriptions requiring the doctor to be called by the pharmacy because of they are not legible. Furthermore, studies have documented that adverse events associated with prescription errors, some resulting in patient death. The system of the present invention addresses these problems, ensuring more secure and accurate fulfillment of prescriptions.

It will be appreciated by those skilled in the art that other variations of the one or more embodiments described herein are possible and may be practised without departing from the scope of the present invention.

What is claimed is:

1. A method for dispensing a drug at an automated dispensary comprising:
   (a) presenting, at the automated dispensary a script for a drug prescribed to a user, the script having a plurality of data elements describing the drug and the user, the data elements including human readable data elements and, optionally, machine readable data elements;
   (b) operating the automated dispensary to scan the data elements;
   (c) reading the scanned data elements to obtain user and drug data;

(d) retrieving, using the drug data:
  a graphical representation of a shape of a pill containing the drug prescribed to the user;
  a graphical representation of a shape of a package containing a plurality of the pills; and
  validation data for the drug prescribed to the user;
(e) performing a validation process based on a comparison of:
  the validation data for the drug prescribed to the user; and
  information about a drug in the automated dispensary to be dispensed to the user;
(f) authorizing the dispensing of the drug in the automated dispensary based on a successful result of the validation process; and
(g) conditional on the authorizing:
  printing a report that includes:
    a result of the comparison of:
      the validation data for the drug prescribed to the user; and
      the information about the drug in the automated dispensary to be dispensed to the user;
    the graphical representation of a shape of a pill containing the drug prescribed to the user;
    the graphical representation of a shape of a package containing a plurality of the pills; and
    instructions to the user to compare:
      the graphical representation of a shape of a pill containing the drug prescribed to the user to the actual shape of a pill in the automated dispensary that is dispensed;
      the graphical representation of a shape of a package containing a plurality of the pills to the actual shape of a package in the automated dispensary that is pending to be dispensed;
  and
  dispensing from the automated dispensary:
    the package in the automated dispensary that is pending to be dispensed; and the printed report.

2. The method of claim 1, the validation process further comprising comparing at least part of the user and drug data with at least part of recorded data being at least one of patient medical history data, patient drug history data, patient identification data, patient insurance data, payment processing data, pedigree data of the drug to be dispensed, and data related to drugs of the same nature as the drug to be dispensed.

3. The method of claim 2, the automated dispensary being a node on a communications network, the network also having at least one other node providing access to the at least one of patient medical history data, patient drug history data, patient identification data, patient insurance data, payment processing data, pedigree data of the drug to be dispensed, and data related to drugs of the same nature as the drug to be dispensed.

4. The method of claim 3, further comprising having a human agent at a node connected to the network read at least some of the scanned elements to obtain at least some of the user and drug data.

5. The method of claim 4, further comprising machine reading at least part of the scanned elements to obtain at least part of the user and drug data.

6. The method of claim 4, further comprising operating the automated dispensary to capture an image of the at least some of the scanned elements, communicating the captured image over the communications network to the human agent.

7. The method of claim 6, wherein the human agent effects a comparison of the read data elements with at least some of the recorded data.

8. The method of claim 7, wherein the human agent effects the authorizing of the dispensing the drug to the user.

9. The method of claim 4, further comprising implementing a link between the human agent and the user, the link being at least one of an audio link and a video link.

10. Apparatus for dispensing a drug to a user comprising:
(a) an automated dispensary;
(b) a presentation station at the automated dispensary for the presentation of a script for a drug prescribed to the user, the script having a plurality of data elements describing the drug and the user, the data elements including human readable data elements and, optionally, machine readable data elements;
(c) a scanning module at the automated dispensary to scan the data elements;
(d) a reading sub-system for reading the scanned data elements to obtain user and drug data;
(e) a retrieving module for using the drug data to retrieve:
  a graphical representation of a shape of a pill containing the drug prescribed to the user;
  a graphical representation of a shape of a package containing a plurality of the pills; and
  validation data for the drug prescribed to the user;
(f) a validation module for performing a validation process based on a comparison of:
  the validation data for the drug prescribed to the user; and
  information about a drug in the automated dispensary to be dispensed to the user;
(g) an authorization module for authorizing the dispensing of the drug in the automated dispensary to be dispensed to the user based on a successful result of the validation process;
(h) a printing module for printing a report that includes:
  a result of the comparison of:
    the validation data for the drug prescribed to the user; and
    the information about the drug in the automated dispensary to be dispensed to the user;
  a graphical representation of a shape of a pill containing the drug prescribed to the user;
  a graphical representation of a shape of a package containing a plurality of the pills; and
  instructions to the user to compare:
    the shape of the package on the report to the actual shape of the package to be dispensed to the user; and
    the shape of the pill on the report to the shape of the pill containing the drug in the automated dispensary to be dispensed to the user;
  and
  a dispensing module for dispensing to the user at the automated dispensary conditional on the authorizing;
    the package containing the plurality of the pills containing the drug prescribed to the user; and
    the printed report.

11. The apparatus of claim 10, the validation module operable to compare at least part of the user and drug data with at least part of recorded data being at least one of patient medical history data, patient drug history data, patient identification data, patient insurance data, payment processing data, pedigree data of the drug to be dispensed, and data related to drugs of the same nature as the drug to be dispensed.

12. The apparatus of claim 11, the automated dispensary being a node on a communications network, the network also having at least one other node providing access to the at least one of patient medical history data, patient drug history data, patient identification data, patient insurance data, payment processing data, pedigree data of the drug to be dispensed, and data related to drugs of the same nature as the drug to be dispensed.

13. The apparatus of claim 12, the reading sub-system including a human agent node connected to the network, and access means to permit a human agent at the human agent node to access and read at least some of the scanned elements to obtain at least some of the user and drug data.

14. The apparatus of claim 13, the reading sub-system further including a machine reading module operable to machine read at least part of the scanned elements to obtain at least part of the user and drug data.

15. The apparatus of claim 13, the scanning module operable to capture an image of the at least some of the scanned elements, the communications network operable to communicate the captured image over the communications network to the human agent.

16. The apparatus of claim 15, further comprising a processing module operable to permit the human agent at the human agent node to effect a comparison of the read data elements with at least some of the recorded data.

17. The apparatus of claim 16, further comprising an authorizing module operable by the human agent to effect the authorizing of the dispensing the drug to the user.

18. The apparatus of claim 13, further comprising a communications link between the human agent node and the automated dispensary, the communications link being at least one of an audio link and a video link.

19. The apparatus of claim 12, wherein the validation process is additionally based on at least one of:
   a history of the humidity at which the drug to be dispensed has been maintained within the automated dispensary;
   a history of the temperature at which the drug to be dispensed has been maintained within the automated dispensary.

20. A method comprising:
(a) receiving at an automated dispensary a script for a drug, the script having a plurality of data elements describing the drug
(b) using the plurality of data elements describing the drug to retrieve:
   a graphical representation of a shape of a pill containing the drug in the scrip;
   a graphical representation of a shape of a package containing a plurality of the pills; and
   validation data for the drug in the script;
(c) performing a validation process based on a comparison of:
   the validation data for the drug in the scrip; and
   information about a drug in the automated dispensary;
(e) authorizing the dispensing of the drug in the automated dispensary based on a successful result of the validation process; and
(f) conditional on the authorizing:
   rendering a report that includes:
      a result of the comparison of:
         the validation data for the drug in the script; and
         the information about the drug in the automated dispensary;
      the graphical representation of a shape of a pill containing the drug in the scrip;
      the graphical representation of a shape of a package containing a plurality of the pills; and
      instructions to compare:
         the graphical representation of a shape of a pill containing the drug in the scrip to the actual shape of a pill in the automated dispensary that is dispensed;
         the graphical representation of a shape of a package containing a plurality of the pills to the actual shape of a package in the automated dispensary that is pending to be dispensed;
   and
   dispensing from the automated dispensary:
      the package in the automated dispensary that is pending to be dispensed; and
      the rendered report.

* * * * *